United States Patent
Meyer (10) Patent No.: US 11,266,522 B2
(45) Date of Patent: Mar. 8, 2022

(54) PESSARY

(71) Applicant: Sally Ann Meyer, Cameron, MO (US)

(72) Inventor: Sally Ann Meyer, Cameron, MO (US)

(*) Notice: Subject to any disclaimer, the term of this patent is extended or adjusted under 35 U.S.C. 154(b) by 444 days.

(21) Appl. No.: 15/998,599

(22) Filed: Aug. 16, 2018

(65) Prior Publication Data

US 2019/0053937 A1 Feb. 21, 2019

Related U.S. Application Data

(60) Provisional application No. 62/546,756, filed on Aug. 17, 2017.

(51) Int. Cl.

| | | |
|---|---|---|
| *A61F 6/08* | (2006.01) | |
| *B29C 33/38* | (2006.01) | |
| *B33Y 10/00* | (2015.01) | |
| *B33Y 80/00* | (2015.01) | |
| *B29L 31/00* | (2006.01) | |
| *B29C 64/118* | (2017.01) | |
| *B29K 91/00* | (2006.01) | |

(52) U.S. Cl.
CPC ............ *A61F 6/08* (2013.01); *B29C 33/3842* (2013.01); *B33Y 10/00* (2014.12); *B33Y 80/00* (2014.12); *B29C 64/118* (2017.08); *B29K 2091/00* (2013.01); *B29L 2031/754* (2013.01)

(58) Field of Classification Search
CPC .. A61F 6/08; A61F 6/12; A61F 2/0004; A61F 2/0009; A61F 2/005; A61F 2/0022; B33Y 10/00; B33Y 80/00; B29C 33/3842; B29C 64/118; B29K 2091/00; B29L 2031/754
See application file for complete search history.

(56) References Cited

U.S. PATENT DOCUMENTS

| | | | |
|---|---|---|---|
| 4,825 A | 10/1846 | Merriman | |
| 1,917,870 A | 7/1933 | Bley | |
| 4,307,716 A | 12/1981 | Davis | |
| 6,503,190 B1 | 1/2003 | Ulmsten et al. | |
| 9,078,726 B2 | 7/2015 | Karapasha | |
| 9,744,630 B2* | 8/2017 | Avery, Jr | A61F 2/005 |
| 2007/0203429 A1* | 8/2007 | Ziv | A61F 2/005 |
| | | | 600/573 |
| 2017/0049609 A1 | 2/2017 | Conti | |

OTHER PUBLICATIONS

Warth, Alvin H. The Chemistry and Technology of Waxes. 1956. pp. 1-943. 2nd Edition. Reinhold Publishing Corporation.
Shearay, Vase Pessary, Jan. 30, 2012, http://youtu.be/0P1v4iNerGA.
Shealray, Suction Vase Pessary, Feb. 2, 2012, http://youtu.be/tc7Fh7ZWUs4.
Whole Woman Village Forum, Feb. 12, 206, 13 pages, https://wholewoman.com/forum/node/495.
Mothering Forums, Jan. 10, 2013 1 page, http://www.mothering.com/forum/502-healing-birth-trauma/1371971-bees-wax-pessary-i-made-work-really-well-me.html.
Zrubek, H., Ginekologia Polska Dec. 1, 1994, 65(12):695-698.

* cited by examiner

*Primary Examiner* — Camtu T Nguyen
(74) *Attorney, Agent, or Firm* — Precipice IP PLLC; Angela J. Grayson (57) ABSTRACT

The present disclosure relates in general to a malleable and non-absorbent pessary having a solid cylindrical body formed of wax for use in improving symptoms associated with pelvic organ prolapse.

20 Claims, 4 Drawing Sheets

PESSARY

CROSS-REFERENCE TO RELATED APPLICATION

This application claims the benefit of priority under 35 U.S.C. § 119 from U.S. Provisional Application Ser. No. 62/546,756 filed Aug. 17, 2017.

FIELD OF INVENTION

The present disclosure relates in general to a malleable and non-absorbent device for use in improving symptoms associated with pelvic organ prolapse.

BACKGROUND OF THE INVENTION

Pelvic Organ Prolapse (POP) and Stress Urinary Incontinence (SUI) is a growing problem for many women. POP and SUI occur when the muscles and tissues supporting the pelvic organs (specifically, the uterus, bladder, or rectum) become weak or loose. When these muscles and tissues are loose, this allows one or more of the pelvic organs to drop or press into or out of the vagina. There are a number of reasons women have POP and SUI symptoms, the principle reason of which is that the muscles and tissues of the uterus loosen with child birth.

Surgical remedies are an option for women who suffer from POP and SUI. In addition, non-surgical options exist such as the use of a pessary device to treat POP and SUI. Pessary devices formed of silicone and other non-naturally derived materials are known. Pessaries formed of silicon and similar materials run the risk of being malodorous after extended use; and potentially contributing to, or causing Silicone Immune Toxicity Syndrome (SITS) for a user. SITS is an immune deficiency disease believed to be caused when silicone is introduced into the body.

Further, many pessaries presently available may not be comfortable for the user. For example, U.S. Pat. No. 6,503,190 provides a pessary device for use in treating POP. The pessary device taught in U.S. Pat. No. 6,503,190 is hollow and coiled, delivering pressure on the urethra to treat incontinence. However coiled apparatuses tend to pinch and cause discomfort for the user. In spite of the forgoing, a need still exists for a customizable pessary with inherent anti-inflammatory properties.

SUMMARY OF THE INVENTION

An embodiment of the invention provides a pessary comprising,
 a) a solid cylindrical body formed of wax and having an outer surface;
 b) the cylindrical body having three sections, a first end, a second end, and a third end wherein the first end and the second end are at opposite ends of the cylindrical body;
 c) the first end forming a first flange extending radially from the first end;
 d) the second end forming a second flange extending radially from the second end;
 e) the third end forming a third flange extending radially from the third end; and wherein;
 f) the first end and the second end each comprise an annular recess in proximity to a perimeter of each said first end and said second end.

Another embodiment of the invention provides the pessary, wherein the first flange and the third flange have substantially the same diameter.

Another embodiment of the invention provides the pessary, wherein the second flange has a smaller diameter than the first flange.

Another embodiment of the invention provides the pessary, wherein the second flange has a smaller diameter than the third flange.

Another embodiment of the invention provides the pessary, wherein the length from the first end to the second end is between 1.25 to 2.50 inches.

Another embodiment of the invention provides the pessary, wherein the length from the first end to the second end is about 1.75 inches.

Another embodiment of the invention provides the pessary, wherein the length from the first end to the second end is about 1.875 inches.

Another embodiment of the invention provides the pessary, wherein the length from the first end to the second end is about 2.0 inches.

Another embodiment of the invention provides the pessary, wherein the first flange has a diameter between 1.25 inches and 2.5 inches.

Another embodiment of the invention provides the pessary, wherein the first flange has a diameter of about 1.75 inches.

Another embodiment of the invention provides the pessary, wherein the first flange has a diameter of about 1.875 inches.

Another embodiment of the invention provides the pessary, wherein the first flange has a diameter of about 2 inches.

Another embodiment of the invention provides the pessary, wherein the second flange has a diameter between 0.75 to 1.125 inches.

Another embodiment of the invention provides the pessary, wherein the second flange has a diameter of about 0.75 inches.

Another embodiment of the invention provides the pessary, wherein the second flange has a diameter of about 1.125 inches.

Another embodiment of the invention provides the pessary, wherein the first flange and the third flange each have a diameter about 1.75 inches and the second flange has a diameter about 1.125 inches, and the length from the first end to the second end is about 1.75 inches.

Another embodiment of the invention provides the pessary, wherein the first flange and the third flange each have diameters about 1.875 inches and the second flange diameter is about 1.125 inches, and the length from the first end to the second end is about 1.875 inches.

Another embodiment of the invention provides the pessary, wherein the first flange and the third flange diameters are each about 2.0 inches and the second flange diameter is about 1.125 inches, and the length from the first end to the second end is about 2.0 inches.

Another embodiment of the invention provides the pessary, wherein the first flange has a first flange annular recess having an inner top diameter and inner bottom diameter, and a recess depth.

An embodiment of the invention provides the first flange annular recess inner top diameter is between about 0.875 inches and about 1.875 inches.

An embodiment of the invention provides the first flange annular recess inner top diameter is about 0.875 inches.

An embodiment of the invention provides the first flange annular recess inner top diameter is about 1 inch.

An embodiment of the invention provides the first flange annular recess inner top diameter is about 1.125 inches.

An embodiment of the invention provides the first flange annular recess inner top diameter is about 1.25 inches.

An embodiment of the invention provides the first flange annular recess inner top diameter is about 1.375 inches.

An embodiment of the invention provides the first flange annular recess inner top diameter is about 1.625 inches.

An embodiment of the invention provides the first flange annular recess inner top diameter is about 1.75 inches.

An embodiment of the invention provides the first flange annular recess inner top diameter is about 1.875 inches.

An embodiment of the invention provides the first flange annular recess inner bottom diameter is between 0.21 and 0.46 inches.

An embodiment of the invention provides the first flange annular recess inner bottom diameter is about 0.21 inches.

An embodiment of the invention provides the first flange annular recess inner bottom diameter is about 0.25 inches.

An embodiment of the invention provides the first flange annular recess inner bottom diameter is about 0.28 inches.

An embodiment of the invention provides the first flange annular recess inner bottom diameter is about 0.30 inches.

An embodiment of the invention provides the first flange annular recess inner bottom diameter is about 0.32 inches.

An embodiment of the invention provides the first flange annular recess inner bottom diameter is about 0.35 inches.

An embodiment of the invention provides the first flange annular recess inner bottom diameter is about 0.40 inches.

An embodiment of the invention provides the first flange annular recess inner bottom diameter is about 0.43 inches.

An embodiment of the invention provides the first flange annular recess inner bottom diameter is about 0.46 inches.

An embodiment of the invention provides the first flange annular recess depth is about 0.30 inches.

An embodiment of the invention provides a pessary for use in improving symptoms associated with pelvic organ prolapse and stress urinary incontinence, comprising:
- a) a solid cylindrical body formed of wax and having an outer surface;
- b) the cylindrical body having three sections, a first end, a second end, and a third end wherein the first end and the second end are at opposite ends of the cylindrical body;
- c) the first end forming a first flange extending radially from the first end;
- d) the second end forming a second flange extending radially from the second end;
- e) the third end forming a third flange extending radially from the third end; and wherein
- f) the first end and the second end each comprise an annular recess in proximity to a perimeter of each said first end and said second end.

An embodiment of the invention provides a method for making a pessary, the method comprising
- a) making a pessary mold, wherein the pessary comprises
  - i. a solid cylindrical body formed of wax and having an outer surface;
  - ii. the cylindrical body having attached thereto three sections, a first end, a second end, and a third end wherein the first end and the second end are at opposite ends of the cylindrical body;
  - iii. the first end forming a first flange extending radially from the first end,
  - iv. the second end forming a second flange extending radially from the second end;
  - v. the third end forming a third flange extending radially from the third end; and wherein
  - vi. the first end and the second end each comprise an annular recess in proximity to a perimeter of each said first end and said second end
- b) filling the mold with hot wax;
- c) cooling the mold of hot wax; and
- d) de-molding the pessary.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this brief summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE FIGURES

Thus, having described the disclosure in the foregoing general terms, reference will now be made to the accompanying drawings, which are not necessarily drawn to scale, and wherein.

DETAILED DESCRIPTION OF THE INVENTION

Some implementations of the present disclosure will now be described more fully hereinafter with reference to the accompanying drawings, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art. For example, unless otherwise indicated, reference to something as being a first, second or the like should not be construed to imply a particular order. Also, for example, reference may be made herein to quantitative measures, values, relationships or the like (e.g., planar, coplanar, perpendicular). Unless otherwise stated, any one or more, if not all, of these may be absolute or approximate to account for acceptable variations that may occur, such as those due to engineering tolerances or the like. Like reference numerals refer to like elements throughout.

The term "solid" means not hollow or containing gaps.

The term "formed" means to make or fashion into a certain shape or arrangement.

The term "wax" means natural or synthetic organic compounds that are lipophilic, malleable solids near ambient temperatures and are low viscosity liquids. These compounds are organic and include higher alkanes and lipids. Wax compounds characteristically consist of long alkyl chains. Waxes may also include various functional groups such as fatty acids, primary and secondary long chain alcohols, unsaturated bonds, aromatics, amides, ketones, and aldehydes. Waxes frequently contain fatty acid esters as well. Waxes are insoluble in water but soluble in organic, nonpolar solvents. Waxes as defined herein include natural wax, waxes from insects, waxes from animals, waxes from plants, waxes from microorganisms, and synthetic waxes. Waxes have a melting point in the range between 40-95° C. See WARTH, ALVIN H. *The Chemistry and Technology of Waxes*. 1956. $2^{nd}$ Edition. Reinhold Publishing Corporation, herein incorporated by reference.

The term "natural wax" means a type wax produced by plants, animals, and insects.

The term "waxes from insects" means beeswax and scale insect wax.

The term "waxes from animals" means wool wax and spermaceti.

The term "waxes from plants" means palm tree waxes, candelilla wax, soy wax, wax, retamo wax, flax wax, cotton wax, hemp wax, sugarcane wax, esparto wax, sorghum-grain wax, rice bran wax, leaf blade waxes, waxes from plat roots, waxes from plant barks, Japan wax (or sumac wax), myrica fruit waxes, cranberry wax, cuticle waxes of fruit, liquid vegetable wax, and floral waxes.

The term "waxes from microorganisms" means waxes in cerebrosides.

The term "synthetic waxes" means long-chain hydrocarbons (alkanes or paraffins) that lack functional groups which is not made from insects, plants, or animals. These waxes are made of ethylene glycol diesters or triesters of long-chain fatty acids ($C_{18}$-$C_{36}$) having a melting point in the range between 60-75° C.

The term "hot" means 40-95° C.

The term "de-mold" means to remove a formed pessary from a mold, for example by holding one side of a mold and pulling the other side of a mold apart to extract a formed pessary.

The term "adjustable" means conformable to a desired dimension by augmenting the original dimensions of the object by not more than 10%.

The term "recess" means a concave region, indentation, or a depression created on an otherwise continuous solid surface.

Example implementations, as described in FIGS. 1-5 of the present disclosure, are directed to a pessary (100) having a solid cylindrical body (112) formed of wax. The wax used to form the pessary (100) can any suitable natural wax, preferably waxes from animals, plants, or insects, and most preferably waxes from bees. The wax from beeswax is most preferable as beeswax has anti-inflammatory properties and is relatively light weight and moldable. Beeswax also provides a highly conformable pessary (100) once inserted in the body due to the physical properties of the wax. Because beeswax is moldable, the pessary (100) also provides the ability for the user to easily adjust the fit (diameter and length of the pessary (100)) within 1%-10% of the original dimensions without changing the overall effectiveness of the device.

The pessary (100) has a cylindrical body (112) as shown in FIGS. 1-5. The cylindrical body (112) has three sections, a first end (118), a second end (120), and a third end (122). The first end (118) and the second end (120) are at opposite ends of the cylindrical body (112). A first end (118) of the pessary (100) forms a first flange (102) which extends radially from the first end (118). A second end (120) of the pessary (100) forms a second flange (104) which extends radially from the second end (120). A third end (122) of the pessary (100) forms a third flange (106) which extends radially from the third end (122).

Figure 1:
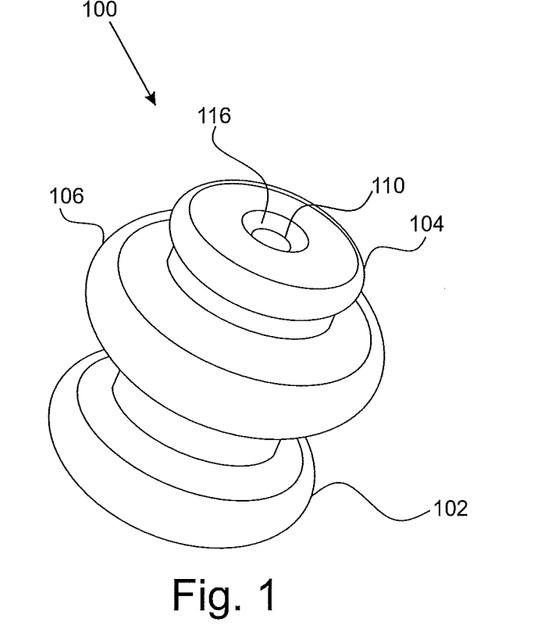
FIG. 1 is a right perspective view of the pessary and showing the second end recess.
Figure 2:
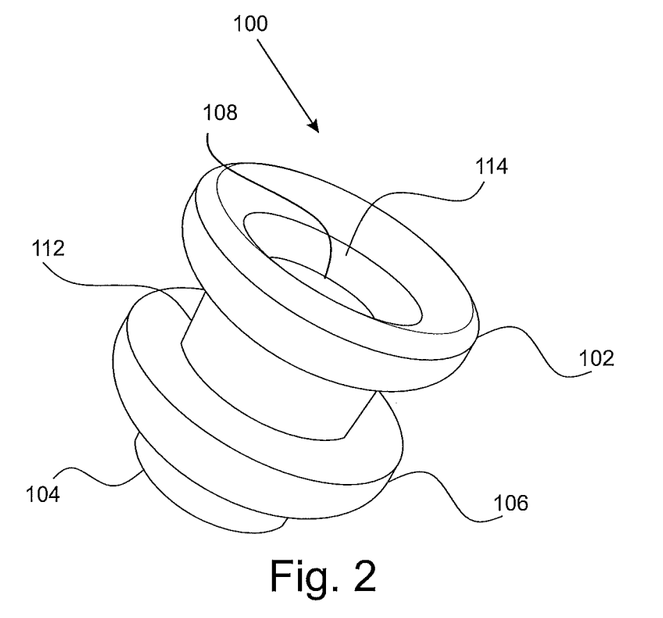
FIG. 2 is a right perspective view of the pessary and showing the first end recess.
Figure 3:
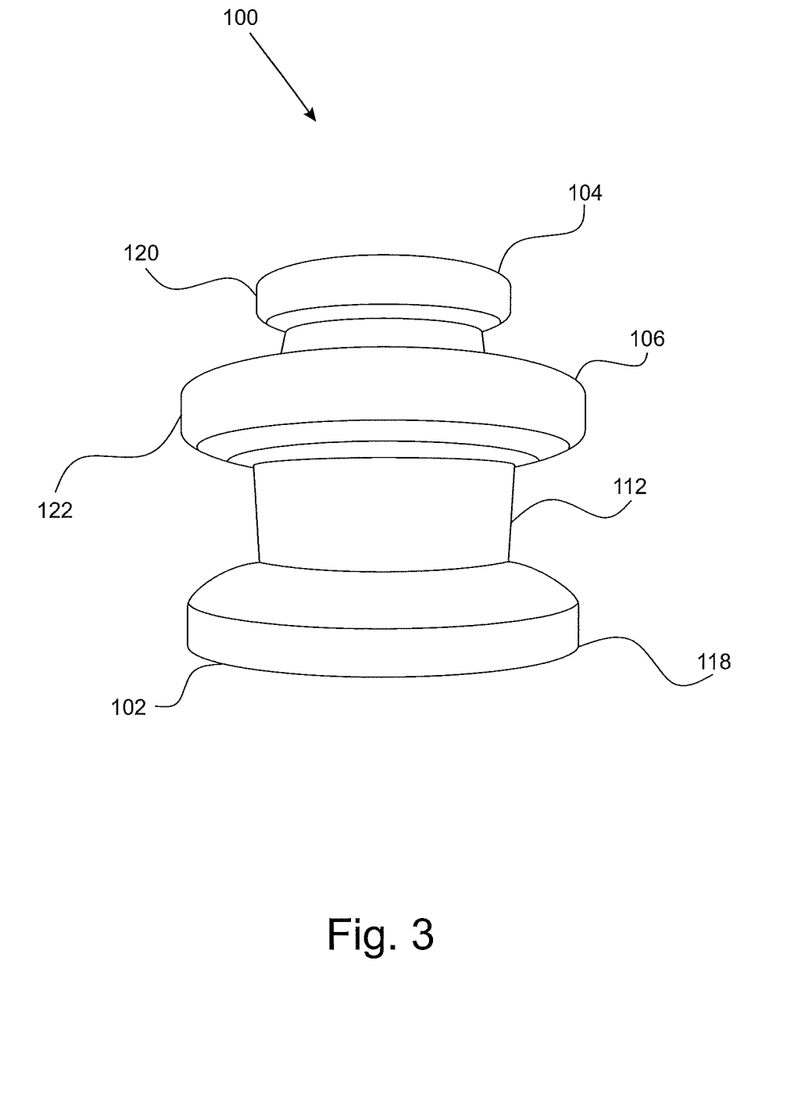
FIG. 3 is front perspective view of the pessary and showing the first flange, the second flange, and the third flange.
Figure 4:
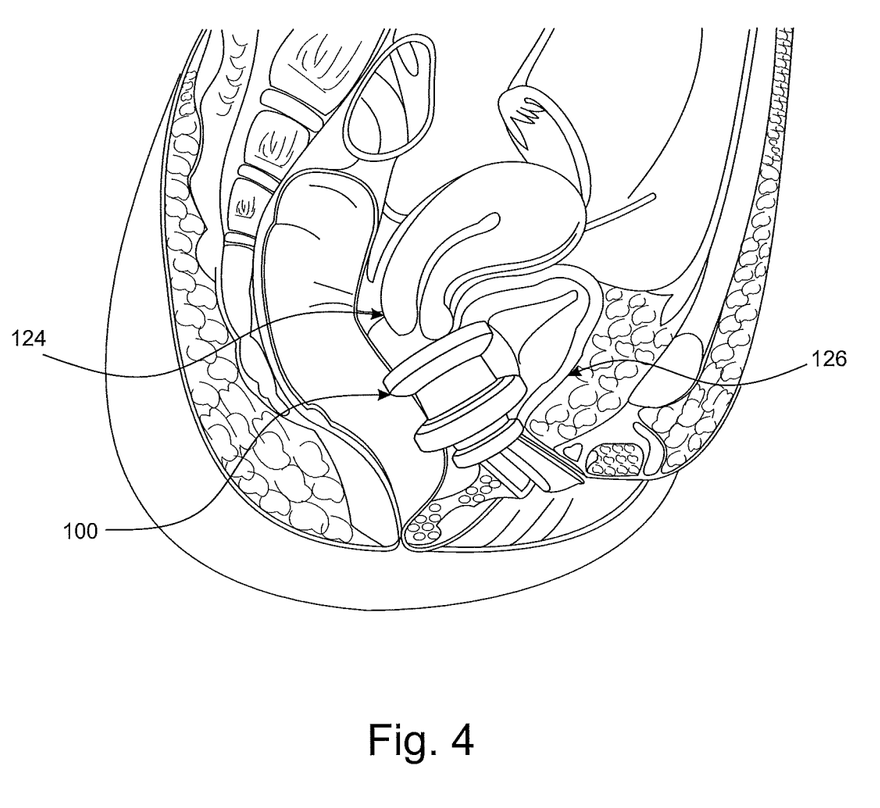
FIG. 4 is a sagittal plane view of the pessary into position in the human body.
Figure 5:
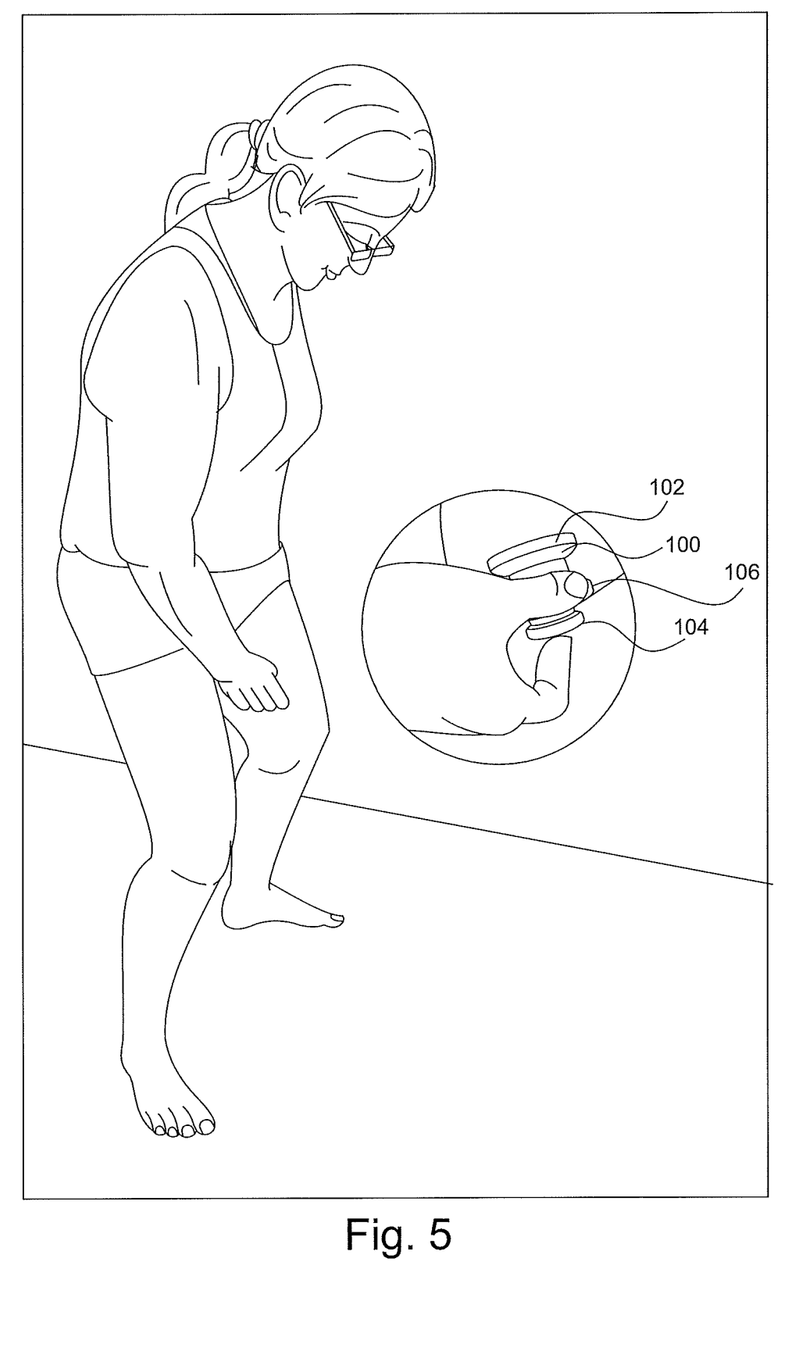
FIG. 5 is an enlarged view of the pessary being inserted in the human body.

The first end (118) of the pessary (100) and the second end (120) of the pessary (100) each comprise an annular recess (formed by a first end recess (108) and a second end recess (110), respectively) in proximity to a perimeter of each first end (118) and second end (120) as shown in FIG. 1 and FIG. 2. The annular recess formed by the first end recess (108) has an annular recess inner top diameter, an annular recess inner bottom diameter, and an annular recess depth. The first end recess (108) is adjacent the pessary cup (114), and the second end recess (110) is adjacent to the pessary button (116). Both the first end recess (108) and the second end recess (110) have a concave configuration. The first end recess (108) is configured to facilitate suctioning the uterus (124) or the cervix to improve fit and stability; the second end recess (110) is configured to complement the tip of a finger (an index finger, for example) and aids in administering the insertion or removal of the pessary (100) into and out of a body through the vaginal canal as shown in FIG. 4 and FIG. 5. The overall design of the pessary (100) is configured to support a prolapsed bladder (126) and to improve and treat the symptoms associated with POP or SUI, as it has been known by those of skill in the art, that a suitably placed object within the vagina proximate to the urethra and/or bladder can be used to support, reposition, and or constrict the urethra and/or bladder to ameliorate incontinence.

The pessary (100) can be made using a variety of methods known to those of skill in the art. For example, the pessary (100) can be made manually or through computer-aided processes.

Manual Pessary Process.

Manual Step One

A wood lathe may be used to create a wooden pessary plug. The wood pessary plug may be constructed out of bass wood, for example. Any suitable wood may be used to construct the wood mold pessary plug that is non-toxic and easy to turn on a lathe.

The pessary (100) may be configured to have the following dimensions in inches:

| Diameter (Overall) | Length (First end to Second End) | First Flange Diameter | Third Flange Diameter | Second Flange Diameter | First Flange Annular Recess Inner Top Diameter | First Flange Annular Recess Inner Bottom Diameter | First Flange Annular Recess Depth |
| --- | --- | --- | --- | --- | --- | --- | --- |
| 1.25" | 1.25" | 1.25" | 1.25" | 0.75" | 0.875" | 0.21" | .30" |
| 1.50" | 1.50" | 1.50" | 1.50" | 0.75" | 1.0" | 0.25" | .30" |
| 1.75" | 1.75" | 1.75" | 1.75" | 1.125" | 1.125" | 0.28" | .30" |
| 1.875" | 1.875" | 1.875" | 1.875" | 1.125" | 1.25" | 0.30" | .30" |
| 2.0" | 2.0" | 2.0" | 2.0" | 1.125" | 1.375" | 0.32" | .30" |
| 2.125" | 2.125" | 2.125" | 2.125" | 1.125" | 1.625" | 0.35" | .30" |
| 2.25" | 2.25" | 2.25" | 2.25" | 1.125" | 1.625" | 0.40" | .30" |
| 2.375" | 2.375" | 2.375" | 2.375" | 1.125" | 1.75" | 0.43" | .30" |
| 2.50" | 2.50" | 2.50" | 2.50" | 1.125" | 1.875" | 0.46" | .30" |

Once the dimensions of the pessary (100) are obtained, the "plug" is then configured having two oversized portions designed to seal the pessary (100) during the mold-making process when the pessary (100) is in the container resulting in a "pessary plug".

The lathe used can be any lathe used by one of ordinary skill in the art to carve wood. For example, a wood lathe from CENTRAL MACHINERY 10"×18" Mini Wood Lathe-Model 65345 distributed by Harbor Freight Tools at 3491 Mission Oaks Blvd., Camarillo, Calif. 93011 may be used.

Once the wooden pessary plug is carved, the pessary plug can be placed in a food-grade container, preferably a food-grade clear plastic container, of suitable height and stability for containing the pessary plug and making a pessary mold. A suitable plastic container is for example a ULINE brand of containers provided by Uline, Inc. 12575 Uline Drive Pleasant Prairie, Wis. 53158.

The plug may be adapted to contain at least two holes or openings. One hole may be adapted for pouring a mold making substance through the plug with the aid of a funnel or similar device. The other hole or opening may be adapted to allow out-gases to escape when a mold making substance is mixed and fully combined. A hole jig can be used to make the holes in suitable positions on the plug, for example close to the edge. The position chosen should allow the mold making substance to stream down the container's edge and fill the container evenly. A suitable mold making substance known to those of reasonable skill in the art may be used such for example SMOOTH ON SMOOTH-SIL silicones 940, 950 and 960 5600 distributed by Smooth-On, Inc. Lower Macungie Road Macungie, Pa. 18062; SIMTEC Silicone distributed by SimTec Silicone Parts, LLC 9658 Premier Pkwy, Miramar, Fla. 33025; or any suitable liquid silicone rubber mold-making material that is food-grade and non-toxic, for example COPYFLEX Liquid Silicone Mold Making Rubber made by Culinart, Inc. 7609 Production Drive, Cincinnati Ohio 45237.

Manual Step Two

The pessary plug can be configured to have a smaller inner ring above a larger outer base ring. The interior of the clear food grade container should fit perfectly, or near perfectly over the smaller inner ring forming a light seal. Specifically, the smaller inner ring should be configured to fit the inner diameter of the container, while the larger outer base ring of the pessary plug should be configured to sit on top of the container, and should match the outer diameter of the container. For example, the outer base ring may have a 3.0 inch diameter while the inner ring diameter may have a diameter about 2.875 inches in the case of a container with an outer diameter of 3 inches and an inner container of 2.875 inches. The inner ring and outer base rings of the pessary plug may deviate from these stated values, as the diameters will depend on the inner and outer diameter of the container chosen.

When utilizing a mold-making substance, it will be important to mix the composition as instructed by the manufacturer. For example, when using COPYFLEX, equal amounts of both catalyst and base are utilized in the set up. Consequently, it will be important to separate mixing utensils until needed, because if utensils are accidently put into the other mixture the mold-making substance can start to set up prematurely, resulting in the loss of an entire batch. In the instant process, water can be used to pre-fill the plastic container and then a measurement can taken of the total volume. The water can be evacuated from the container and equal parts catalysts and equal parts base can the added to the container in proportion to the total volume of the container.

An optional step of placing a layer of lubricant, for example olive oil, along the entire interior of the clear plastic container to allow the mold to slip out easier.

The mold-making substance should be streamed slowly into the clear container to eliminate air bubbles from forming in the mold-making substance. Air bubbles should be avoided, as the air bubbles can get trapped and can ruin the finished pessary (100) product.

Manual Step Three

Once the mold-making substance has been added to the container, the mold can set up from 4 to 36 hours. The length of set up time will depend on the mold-making product chosen. Once set, the mold can be extracted from the plastic container.

Manual Step Four

Once the mold-mold making substance has set creating the mold, the pessary plug can be separated from the wood pessary plug. To extract the wooden pessary plug, a line should be cut with a sharp clean knife, down both sides of the mold with care. One should start with where the wood base plug begins and work down and along each side. One should not cut the mold entirely in half, but rather should leave the mold together at the bottom, keeping the halves aligned. Once cuts have been established large enough to extract the wooden pessary plug, the plug should be removed.

Manual Step Five

Another clear container of suitable width and depth to loosely but securely hold the mold can be utilized. The mold should be placed into the container and pushed until the mold is leveled with the container top.

Manual Step Six

A wax melter with a suitable means for pouring melted wax should be filled with at least two ounces of wax, for example, substantially pure organic bees wax. Beeswax can be obtained in from any suitable distributor or supplier. A suitable supplier is, for example, Grateful Shed Antler Chews, 146 N 4668 E, Rigby Id. 83442. A suitable wax melter is, for example, the Presto Wax Melter. The melter should be set to "warm" the wax, (from 40 to 95 degrees Celsius), allowing the wax to melt. The wax should not be permitted to boil, but simply melt to a consistency that makes pouring lump-free wax possible.

Manual Step Seven

Place mold under the melter's faucet or other means of extraction, and decant until just a little wax comes out at one time, but slowly. A slow steady stream should be utilized to keep air bubbles from forming in the wax. Parchment cooking paper can be placed under the extraction means to catch any dripped wax. One of reasonable skill in the art can locate parchment paper in any well-stocked grocery store.

Manual Step Eight

Once the mold has been filled, the mold should be kept immobile and allowed to cool for at least an hour before de-molding. Once cooled, the pessary (100) should be de-molded.

Manual Step Nine

The newly formed pessary (100) can be placed in a storage container for safe keeping until ready to use.

Computer-Aided Pessary Process.

The pessary (100) can be made utilizing any suitable 3-D printer with the aid of a any suitable 3-D printer software to create the pessary mold. Food-grade safe materials should be used in all steps when manufacturing the pessary (100). 3-D software can range from the beginner to engineering levels of expertise. An example of a suitable 3-D software suite is AUTODESK 123D distributed by Autodesk, Inc. 111 McInnis Parkway San Rafael Calif. 94903. Another example of a suitable 3-D software suite is TURBOCAD 3D design software, distributed by IMSI Design LLC 64 Digital Drive Suite 200 Novato Calif. 94949.

3-D printer filaments should be food-grade safe. An example of an FDA certified food-safe filament is a product called T-GLASE, manufactured by taulman3D 4053C-D N. Saint Peters Parkway Saint Peters Mo. 63376

A suitable 3-D printer with a stainless-steel nozzle capable of utilizing the T-GLASE filament should be used. For example, a suitable 3-D printer is MAKERGEAR brand 3-D printers manufactured by MakerGear, LLC 23632 Mercantile Rd. Unit G Beachwood, Ohio 44122 USA.

Computer-Aided Step One

Using software, the pessary (100) can be designed by layering primitives (objects) already defined in the software, with the desired dimensions of the pessary (100) needed.

The pessary (100) may be configured to have the following dimensions in inches:

| Diameter (Overall) | Length (First end to Second End) | First Flange Diameter | Third Flange Diameter | Second Flange Diameter | First Flange Annular Recess Inner Top Diameter | First Flange Annular Recess Inner Bottom Diameter | First Flange Annular Recess Depth |
|---|---|---|---|---|---|---|---|
| 1.25" | 1.25" | 1.25" | 1.25" | 0.75" | 0.875" | 0.21" | .30" |
| 1.50" | 1.50" | 1.50" | 1.50" | 0.75" | 1.0" | 0.25" | .30" |
| 1.75" | 1.75" | 1.75" | 1.75" | 1.125" | 1.125" | 0.28" | .30" |
| 1.875" | 1.875" | 1.875" | 1.875" | 1.125" | 1.25" | 0.30" | .30" |
| 2.0" | 2.0" | 2.0" | 2.0" | 1.125" | 1.375" | 0.32" | .30" |
| 2.125" | 2.125" | 2.125" | 2.125" | 1.125" | 1.625" | 0.35" | .30" |
| 2.25" | 2.25" | 2.25" | 2.25" | 1.125" | 1.625" | 0.40" | .30" |
| 2.375" | 2.375" | 2.375" | 2.375" | 1.125" | 1.75" | 0.43" | .30" |
| 2.50" | 2.50" | 2.50" | 2.50" | 1.125" | 1.875" | 0.46" | .30" |

The pessary (100) can made from the cylinder (primitive) and the cone (primitive). The cylinders can be stacked on top of each other with their respective dimensions, and through utilizing the Boolean method of subtract, the cone (primitive) is taken out of the cylinder. The completed stack can then be combined as one device using the Boolean method of add to create a computer-aided pessary (100) of the desired dimensions.

Computer-Aided Step Two

Once the computer-aided pessary (100) design is completed, attention should be then turned to making the pessary plug. The pessary plug dimensions are substantially similar to the pessary (100), with the exception that the plug has a small opening at one of the ends which configured to received wax by a funnel or similar decanting aid. The pessary plug can be made by computer-aided processes and utilizing the Boolean add/subtract technique.

Computer-Aided Step Three

The resulting pessary mold can be split in half, by using a splice method known to one of skill in the art. The mold should be kept together exactly so an alignment key can be made by computer-aided processes.

For alignments keys, the Boolean add/subtract technique can be utilized. Alignment keys must be exactly on the mold center split.

Computer-Aided Step Four

A wax melter with a suitable means for pouring melted wax should be filled with at least two ounces of wax, for example, substantially pure organic beeswax. Beeswax can be obtained in from any suitable distributor or supplier. A suitable supplier is, for example, Grateful Shed Antler Chews, 146 N 4668 E, Rigby Id. 83442. A suitable wax melter is for example the Presto Wax Melter. The melter should be set to "warm" (from 40 to 95 degrees Celsius), allowing the wax to melt. The wax should not be permitted to boil, but simply melt to a consistency that makes pouring lump-free wax possible.

Computer-Aided Step Five

Place mold under the melter's faucet or other means of extraction, and decant until just a little wax comes out at one time, but slowly. A slow steady stream should be utilized to keep air bubbles from forming in the wax. Parchment cooking paper can be placed under the extraction means to catch any dripped wax. One of reasonable skill in the art can locate parchment paper in any well-stocked grocery store.

Computer-Aided Step Six

Once the mold has been filled, the mold should be kept immobile and allowed to cool for at least an hour before de-molding. Once cooled, the pessary (100) should be de-molded.

Computer-Aided Step Seven

The newly formed pessary (100) can be placed in a storage container for safe keeping until ready to use.

Many modifications and other implementations of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific implementations disclosed, and that modifications and other implementations are intended to be included within the scope of the appended claims.

Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims.

Although specific terms are employed herein, they are used in a generic and descriptive sense only and not for purposes of limitation.

I claim:

1. A pessary comprising:
   a) a solid cylindrical body formed of wax and having an outer surface;
   b) the cylindrical body having three sections, a first end, a second end, and a third end wherein the first end and the second end are at opposite ends of the cylindrical body;
   c) the first end forming a first flange extending radially from the first end;
   d) the second end forming a second flange extending radially from the second end;
   e) the third end forming a third flange extending radially from the third end; and wherein
   f) the first end and the second end each comprise an annular recess in proximity to a perimeter of each said first end and said second end.

2. The pessary of claim 1, wherein the first flange and the third flange have substantially the same diameter.

3. The pessary of claim 1, wherein the second flange has a smaller diameter than the first flange.

4. The pessary of claim 1, wherein the second flange has a smaller diameter than the third flange.

5. The pessary of claim 1, wherein the length from the first end to the second end is between 1.25 to 2.50 inches.

6. The pessary of claim 1, wherein the length from the first end to the second end is about 1.75 inches.

7. The pessary of claim 1, wherein the length from the first end to the second end is about 1.875 inches.

8. The pessary of claim 1, wherein the length from the first end to the second end is about 2.0 inches.

9. The pessary of claim 1, wherein the first flange has a diameter between 1.25 inches and 2.5 inches.

10. The pessary of claim 1, wherein the first flange has a diameter of about 1.75 inches.

11. The pessary of claim 1, wherein the first flange has a diameter of about 1.875 inches.

12. The pessary of claim 1, wherein the first flange has a diameter of about 2 inches.

13. The pessary of claim 1, wherein the second flange has a diameter between 0.75 to 1.125 inches.

14. The pessary of claim 1, wherein the second flange has a diameter of about 0.75 inches.

15. The pessary of claim 1, wherein the second flange has a diameter of about 1.125 inches.

16. The pessary of claim 1, wherein the first flange and the third flange each have a diameter about 1.75 inches, and the second flange has a diameter about 1.125 inches, and the length from the first end to the second end is about 1.75 inches.

17. The pessary of claim 1, wherein the first flange and the third flange each have a diameter about 1.875 inches, and the second flange has a diameter about 1.125 inches, and the length from the first end to the second end is about 1.875 inches.

18. The pessary of claim 1, wherein the first flange and the third flange each have a diameter about 2.0 inches and the second flange has a diameter about 1.125 inches, and the length from the first end to the second end is about 2.0 inches.

19. A pessary for use in improving symptoms associated with pelvic organ prolapse and stress urinary incontinence, comprising:
   a) a solid cylindrical body formed of wax and having an outer surface;
   b) the cylindrical body having three sections, a first end, a second end, and a third end wherein the first end and the second end are at opposite ends of the cylindrical body;
   c) the first end forming a first flange extending radially from the first end;
   d) the second end forming a second flange extending radially from the second end;
   e) the third end forming a third flange extending radially from the third end; and wherein
   f) the first end and the second end each comprise an annular recess in proximity to a perimeter of each said first end and said second end.

20. A method for making a pessary, the method comprising:
   a. making a pessary mold, wherein the pessary comprises
      i. a solid cylindrical body formed of wax and having an outer surface;
      ii. the cylindrical body having attached thereto three sections, a first end, a second end, and a third end wherein the first end and the second end are at opposite ends of the cylindrical body;
      iii. the first end forming a first flange extending radially from the first end,
      iv. the second end forming a second flange extending radially from the second end;
      v. the third end forming a third flange extending radially from the third end; and wherein
      vi. the first end and the second end each comprise an annular recess in proximity to a perimeter of each said first end and said second end
   b. filling the mold with hot wax;
   c. cooling the mold of hot wax; and
   d. de-molding the pessary.

* * * * *